(12) United States Patent
Rogerson

(10) Patent No.: US 7,204,247 B1
(45) Date of Patent: *Apr. 17, 2007

(54) OXYGEN DELIVERY SYSTEM

(75) Inventor: L. Keith Rogerson, #9 Fourth Ave., Isle of Palms, SC (US) 29451

(73) Assignee: L. Keith Rogerson, Isle of Palms, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/364,232

(22) Filed: Feb. 28, 2006

Related U.S. Application Data

(63) Continuation of application No. 10/295,676, filed on Nov. 15, 2002, now Pat. No. 7,051,731.

(51) Int. Cl.
  *A62B 7/02* (2006.01)
  *A61M 15/00* (2006.01)
  *A61M 16/00* (2006.01)

(52) U.S. Cl. .............. 128/200.23; 128/203.12; 128/204.18

(58) Field of Classification Search ............ None
  See application file for complete search history.

(56) References Cited

U.S. PATENT DOCUMENTS

| | | | |
|---|---|---|---|
| 4,996,982 A | 3/1991 | Williamson | |
| 5,209,225 A | 5/1993 | Glenn | |
| 5,224,472 A | 7/1993 | Pesenti et al. | |
| 5,263,475 A | 11/1993 | Altermatt et al. | |
| 5,605,148 A | 2/1997 | Jones | |
| 5,653,223 A | 8/1997 | Pruitt | |
| 5,655,525 A | 8/1997 | Orr | |
| 5,750,077 A | 5/1998 | Schoen | |
| 5,979,442 A | 11/1999 | Orr | |
| 6,143,251 A | 11/2000 | Beller et al. | |
| 6,401,714 B1 | 6/2002 | Giorgini | |
| 7,051,731 B1 * | 5/2006 | Rogerson | 128/200.23 |

* cited by examiner

*Primary Examiner*—Glenn K. Dawson
(74) *Attorney, Agent, or Firm*—Dority & Manning P.A.

(57) ABSTRACT

A portable gas delivery system is provided to provide oxygen or other gaseous mixture for use in emergencies, athletic events, and similar activities. The portable gas delivery system includes a regulator with an accumulator chamber disposed within the regulator and adjacent a mixing chamber. The accumulator chamber receives oxygen or other gas from a replaceable gas source such as a cylinder. The mixing chamber mixes ambient air and gas from the cylinder to form a gaseous mixture which is inhaled by a user. Each use of the portable gas delivery system may be in metered burst of predetermined duration and/or frequency or may be substantially continuous as provided for in the accompanying method.

10 Claims, 4 Drawing Sheets

OXYGEN DELIVERY SYSTEM

RELATED APPLICATIONS

The present application is a continuation application of U.S. application Ser. No. 10/295,676 filed Nov. 15, 2002 now U.S. Pat. No. 7,051,731, and claims priority thereto.

BACKGROUND OF THE INVENTION

Conventional portable breathing devices are known which range from emergency breathing apparatuses to nebulizers for delivering inhalated aerosolized medications. For instance, Orr (U.S. Pat. No. 5,979,442) discloses an emergency breathing apparatus having a mouthpiece attached to an oxygen container, and includes a decorative front portion attachable to the oxygen container. Williamson (U.S. Pat. No. 4,996,982) discloses a portable emergency breathing apparatus with a mouthpiece, regulator, air storage container, and a holster for storing the apparatus when not in use. Pruitt (U.S. Pat. No. 5,653,223) adapts a nebulizer to a standard oxygen delivery tank to deliver metered quantities of nebulized liquid medication.

In general, the conventional breathing devices suffer from limitations unique to small portable applications. In many instances, the known breathing devices utilize potentially hazardous chemicals. For example, several chemical systems have been developed, mainly for commercial aircraft use, that create oxygen via an exothermic reaction. The exothermic reaction couples with a reaction in which sodium chlorate is decomposed to oxygen and sodium chloride. These systems can be inadvertently activated by mechanical agitation, and also require very high temperatures for the decomposition reaction.

In other instances, the conventional breathing devices suffer from complicated constructions requiring, for instance, adapters, connectors, reagent chambers, masks, and metering mechanisms for powdered or liquid medications for mixing with oxygen or ambient air. In particular, many conventional breathing devices, designed to supply oxygen, require separate oxygen accumulator chambers located apart from their regulators. Such devices are suitable for stationary settings such as in aircraft or hospitals but are cumbersome in dynamic settings.

BRIEF SUMMARY OF THE INVENTION

In general, the present invention provides a portable gas delivery system, and a method of using the portable gas delivery system. The component parts of the portable gas delivery system are simple, reliable, and economical to manufacture and use. Other aspects and advantages of the invention will be apparent from the following description and the attached drawings, or can be learned through practice of the invention.

According to an aspect of the present invention, the portable gas delivery system includes an accumulator chamber disposed within a regulator with a mixing chamber located adjacent to the accumulator chamber. The accumulator chamber is constructed for receipt of a gas such as oxygen in a substantially continuous flow or in bursts having predetermined duration and/or frequency. The oxygen is mixable with an ambient air in the mixing chamber and inhalable by a user. This arrangement satisfies a significant need for a device that is simple, economical to manufacture and use, and effective for supplying air or oxygen in athletic, emergency, recreational and similar settings.

In one aspect, a cartridge, cylinder, or similar gas-containing device is removably and replaceably attachable to the regulator of the invention. The gas may be oxygen or an oxygen-flavorant combination. The flavorant can be a variety of flavorings such as orange, cherry, peppermint, and spearmint, depending on the user's preference.

According to another aspect of the invention, the portable gas delivery system is portably carried in a coat pocket, shirt pocket, pants pocket or the like. For example, the portable gas delivery system is sufficiently compact for use by athletes such as snow-skiers, mountain-climbers, runners and the like for refreshment or by necessity. Moreover, the portable gas delivery system is suited for use in fashionable "oxygen bars," which are typically located in metropolitan areas that may have pollution or smog problems. Oxygen bar patrons can use the portable gas delivery system in the oxygen bar and/or purchase it for subsequent use.

More particularly, in one embodiment of the invention, a portable gas delivery system includes a regulator having an accumulator chamber therein and a mixing chamber, the accumulator chamber configured to receive a gas, the mixing chamber in gaseous communication with the accumulator chamber and configured to form a gaseous mixture with the gas from the accumulator chamber by mixing in an ambient air; means for discretely filling the accumulator chamber with the gas; and an outlet in communication with the mixing chamber, configured to deliver the gaseous mixture from the mixing chamber. In this embodiment, the accumulator chamber is at least two cubic inches, and the gas is oxygen, or the gas is oxygen and a flavorant. The flavorant is selected from the orange, lemon-lime, grape, cherry, strawberry, peppermint, mint, spearmint, licorice, bubble-gum, blackberry, blueberry, apple, banana, kiwi, lime, lemon, watermelon, pina colada, and combinations of these flavorants.

Also in this embodiment, the means for discretely filling the accumulator chamber includes a regulating diaphragm defining a hole therethrough and biasing means for biasing valve means for opening and filling the accumulator chamber with the gas via the hole. The biasing means for biasing is a spring and a slide mechanism, the spring disposed within the regulator and operably connected to the slide mechanism such that operation of the slide mechanism presses the spring against the valve means to open the accumulator chamber.

Further in this embodiment, the valve means includes devices selected from the group consisting of a Strater valve, a disc assembly, a ball valve assembly, and combinations of these devices.

Also in this embodiment, the mixing chamber defines a vent therethrough for receiving the gas from the accumulator chamber.

This embodiment also includes a cap attachable to the mixing chamber, the cap defining a breather slot therethrough, the breather slot configured to deliver the ambient air to the mixing chamber to mix with the gas from the accumulator chamber to form the gaseous mixture. The cap and the mixing chamber form a mouthpiece with the outlet disposed on the mouthpiece. The cap and the mixing chamber can be formed unitarily by injection molding.

This embodiment further includes a cartridge attachable to the regulator, the cartridge containing the gas and configured to deliver the gas to the accumulator chamber. This embodiment also includes cartridge receiver means for replaceably attaching the cartridge to the regulator. The cartridge receiver means can be attached to the accumulator chamber apart from the mixing chamber, the cartridge receiver means including a thread assembly for receiving threads defined on the cartridge.

This embodiment also includes a cartridge access device configured to access the gas in the cartridge when the cartridge is received by the thread assembly. The cartridge access device can be a pin configured to puncture a portion of the cartridge to permit the gas to exit the cartridge. The cartridge can be from between 2 inches to about 5 inches in height and from between 1 inch to about 2 inches in diameter. Moreover, the cartridge can be from between 50 cubic inches to less than 90 cubic inches. A flow rate of this embodiment is from between 1.5 liters per minute to about 2.5 liters per minute.

Moreover, this embodiment of the gas delivery system can include a cylinder cover removably attachable to the regulator. The gas delivery system with cylinder cover is from between 3 inches to about 6 inches high and from between 1.5 inches to about 2.5 inches in diameter.

In another embodiment of invention, an oxygen delivery system includes a regulator having an accumulator chamber therein and a breathing outlet component disposed adjacent the accumulator chamber, the accumulator chamber configured to receive oxygen from a cartridge removably attachable to the regulator, the breathing outlet component configured to form a gaseous mixture with the oxygen from the accumulator chamber and an ambient air from external the oxygen delivery system, the breathing outlet component having an outlet therein to deliver the gaseous mixture externally; and a valve assembly attached to the regulator and configured for discretely filling the accumulator chamber. The breathing outlet component can include a mixing chamber with a vent therethrough configured to receive the gas from the accumulator chamber.

This embodiment can also include a cap attachable to the breathing outlet component, the cap defining a breather slot therethrough, the breather slot configured to deliver the ambient air to the mixing chamber to mix with the oxygen from the accumulator chamber to form the gaseous mixture. The cap can be mated with the breathing outlet component by an attachment selected from the group consisting of unitary injection mold, snap-fit, slide-fit, press-fit, or combinations of these fittings with the mated cap and the breathing outlet component forming a mouthpiece.

Also in this embodiment, the accumulator chamber is at least two cubic inches, and a gaseous flavorant is mixed with the oxygen. The flavorant can be selected from orange, lemon-lime, grape, cherry, strawberry, peppermint, mint, spearmint, licorice, bubble-gum, blackberry, blueberry, apple, banana, kiwi, lime, lemon, watermelon, piná colada, and combinations of these flavorants.

Further in this embodiment, the valve assembly includes devices selected from the group consisting of a Strater valve, a disc assembly, a ball valve assembly, and combinations of these devices, and further includes a spring and a slide mechanism, the spring disposed within the regulator and operably connected to the slide mechanism such that operation of the slide mechanism presses the spring against the valve assembly to open the accumulator chamber.

The cartridge in this embodiment is from between 2 inches to about 5 inches in height and from between 1 inch to about 2 inches in diameter. Also, the cartridge is from between 50 cubic inches to less than 90 cubic inches. A flow rate of the gas delivery system is from between 1.5 liters per minute to about 2.5 liters per minute.

This embodiment also includes a cylinder cover removably attachable to the regulator. The cylinder cover is from between 3 inches to about 6 inches high and from between 1.5 inches to about 2.5 inches in diameter.

According to the invention, a method of discretely filling an oxygen delivery system with measured quantities of oxygen is also provided. The method includes the steps of a) providing the oxygen delivery system with a regulator having an accumulator chamber therein and a breathing outlet component disposed adjacent the accumulator chamber, the accumulator chamber configured to receive oxygen from a cartridge via a valve assembly attached to the regulator, the cartridge removably attachable to the regulator, the breathing outlet component configured to form a gaseous mixture with the oxygen from the accumulator chamber and an ambient air from external the oxygen delivery system, the breathing outlet component having an outlet therein to deliver the gaseous mixture externally; b) activating a valve assembly actuator disposed on the oxygen delivery system to controllably fill the accumulator chamber with oxygen, the valve assembly actuator operably connected to the valve assembly and configured to controllably bias the valve assembly to an open position to open an aperture in the accumulator chamber to permit oxygen from the cartridge to enter the accumulator chamber; and c) inhaling the oxygen from the accumulator chamber, the step of inhaling simultaneously drawing the ambient air into the breathing outlet component and forming the gaseous mixture.

According to the method of discretely filling an oxygen delivery system, controllably filling the accumulator chamber can include the substeps of activating the valve assembly actuator for a predetermined time and deactivating; presetting the valve assembly actuator to deliver a measured quantity of oxygen; and combinations of these substeps.

The cartridge used in the method is from between 2 inches to about 5 inches in height and from between 1 inch to about 2 inches in diameter, and the cartridge is from between 50 cubic inches to less than 90 cubic inches. A flow rate of the oxygen delivery system is from between 1.5 liters per minute to about 2.5 liters per minute.

Also according to the method, a cylinder cover is provided, which is removably attachable to the regulator. The cylinder cover is from between 3 inches to about 6 inches high and from between 1.5 inches to about 2.5 inches in diameter.

The method may also include providing a flavorant mixed with the oxygen. The flavorant can be orange, lemon-lime, grape, cherry, strawberry, peppermint, mint, spearmint, licorice, bubble-gum, blackberry, blueberry, apple, banana, kiwi, lime, lemon, watermelon, piná colada, and combinations of these flavorants.

The breathing outlet component according to the method includes a cap and a mixing chamber the cap attachable to the mixing chamber, the cap defining a breather slot therethrough, the breather slot configured to deliver the ambient air to the mixing chamber to mix with the gas from the accumulator chamber to form the gaseous mixture.

Also according to the method, the cap and the mixing chamber are formed by a step selected from the group consisting of injection molding, blow-molding, extension-molding, press-molding, and combinations of these steps.

In yet another embodiment according to the disclosure, a portable gas delivery system includes a regulator having a mixing chamber and an accumulator chamber therein, the accumulator chamber being at least 0.2 cubic inches in volume; a cartridge attachable to the regulator, the cartridge containing a gas and configured to deliver the gas to the accumulator chamber at a flow rate of at least about 1.5 liters per minute, the mixing chamber in gaseous communication with the accumulator chamber and configured to form a gaseous mixture with the gas from the accumulator chamber by mixing in an ambient air; means for filling the accumulator chamber with the gas; and an outlet in communication with the mixing chamber, the outlet being configured to deliver the gaseous mixture from the mixing chamber. In this aspect, the gas may be oxygen and a flavorant.

The means for filling the accumulator chamber in this aspect of the disclosure may include a regulating diaphragm defining a hole therethrough and biasing means for biasing valve means for opening and filling the accumulator chamber with the gas via the hole. The biasing means for biasing may be a spring and a slide mechanism. The spring may be disposed within the regulator and operably connected to the slide mechanism such that operation of the slide mechanism presses the spring against the valve means to open the accumulator chamber. Also, the means for filling the accumulator chamber may include a metering mechanism configured to deliver a metered dosage of the gas to the accumulator chamber.

In a further embodiment of the disclosure, an individual use gas delivery system includes a regulator having an accumulator chamber and a breathing outlet component, the accumulator being at least 0.15 cubic inches in volume, the breathing outlet component disposed adjacent the accumulator chamber; a replaceable cartridge attachable to the regulator, the accumulator chamber configured to receive a quantity of oxygen from the cartridge, the breathing outlet component configured to form a gaseous mixture with the oxygen from the accumulator chamber and ambient air disposed about the gas delivery system, the breathing outlet component having an outlet therein to deliver the gaseous mixture to a user; and a valve assembly attached to the regulator and configured for filling the accumulator chamber.

In this aspect, the breathing outlet component includes a mixing chamber therein with a vent therethrough configured to receive the oxygen from the accumulator chamber. The oxygen may be mixed with a flavorant such as orange, lemon-lime, grape, cherry, strawberry, peppermint, mint, spearmint, licorice, bubble-gum, blackberry, blueberry, apple, banana, kiwi, lime, lemon, watermelon, piná colada, and combinations thereof.

Also in this aspect of the disclosure, the valve assembly can be manually operated and include a spring and a slide mechanism configured to open the accumulator chamber, the spring being configured to urge closed the accumulator chamber. The valve assembly may a metering mechanism configured to deliver a metered dosage of the oxygen to the accumulator chamber.

Other features and aspects of the present invention are discussed in greater detail below.

BRIEF DESCRIPTION OF THE DRAWINGS

The above and other aspects and advantages of the present invention are apparent from the detailed description below in combination with the drawings, in which.

DETAILED DESCRIPTION OF THE INVENTION

Detailed reference will now be made to the drawings in which examples embodying the present invention are shown. The drawings and detailed description provide a full and detailed written description of the invention and the manner and process for making and using it so as to enable one skilled in the pertinent art to make and use it. The drawings and detailed description also provide the best mode of carrying out the invention. However, the examples set forth herein are provided by way of explanation of the invention and are not meant as limitations of the invention. The present invention thus includes modifications and variations of the following examples as come within the scope of the appended claims and their equivalents.

Figure 1:
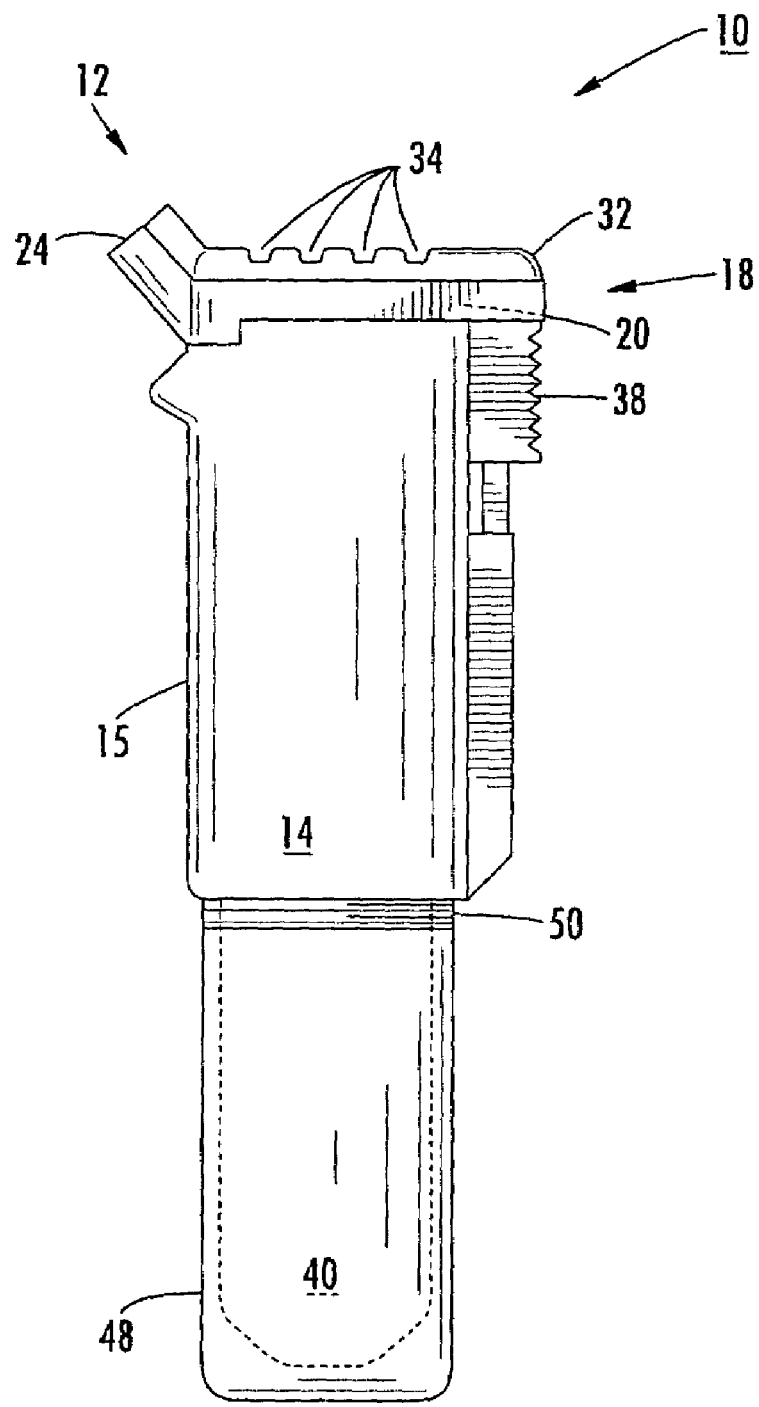
FIG. 1 is a side-view of an embodiment of a portable gas delivery system according to an aspect of the present invention.

The Figures generally show a portable gas delivery system identified by the numeral 10. The portable gas delivery system 10 includes a mouthpiece 12 attached to a regulator 14. A cylinder or cartridge 40 containing a gas such as oxygen $O_2$ is attached to the regulator 14. FIG. 1 further shows that the regulator 14 has a regulator body 15 to which a cartridge cover 48 is optionally attached to cover the cartridge 40 for aesthetic or protective purposes.

The cartridge 40 may be cylindrically shaped, as shown, and approximately 2 to 5 inches long, between 1 to about 2 inches in diameter, and hold approximately 50 cubic inches to about 90 cubic inches of compressed oxygen $O_2$. The cartridge 40 provides a flow rate of between 1.5 liters per minute to about 2.5 liters per minute of oxygen $O_2$ and potentially other gases or particulates. For instance, the gas in the cartridge 40 can include various mixtures such as nitrogen, hydrogen, aerosolized medicines, flavorants and similar additives. It should be understood that various other cartridges may be used with the present invention other than the examples shown. For instance, the cartridge 40 can be square, rectangular, round or other shapes and be larger or smaller with respectively larger or smaller cubic volumes.

As illustrated in FIG. 1, the mouthpiece 12 has a breathing outlet component 18, which includes a mixing chamber 20, a vent 22 and at least part of an outlet 24 (alternatively, tube or conduit). A cap 32 is disposed on the breathing outlet component 18 to form the mouthpiece 12.

Figure 2:
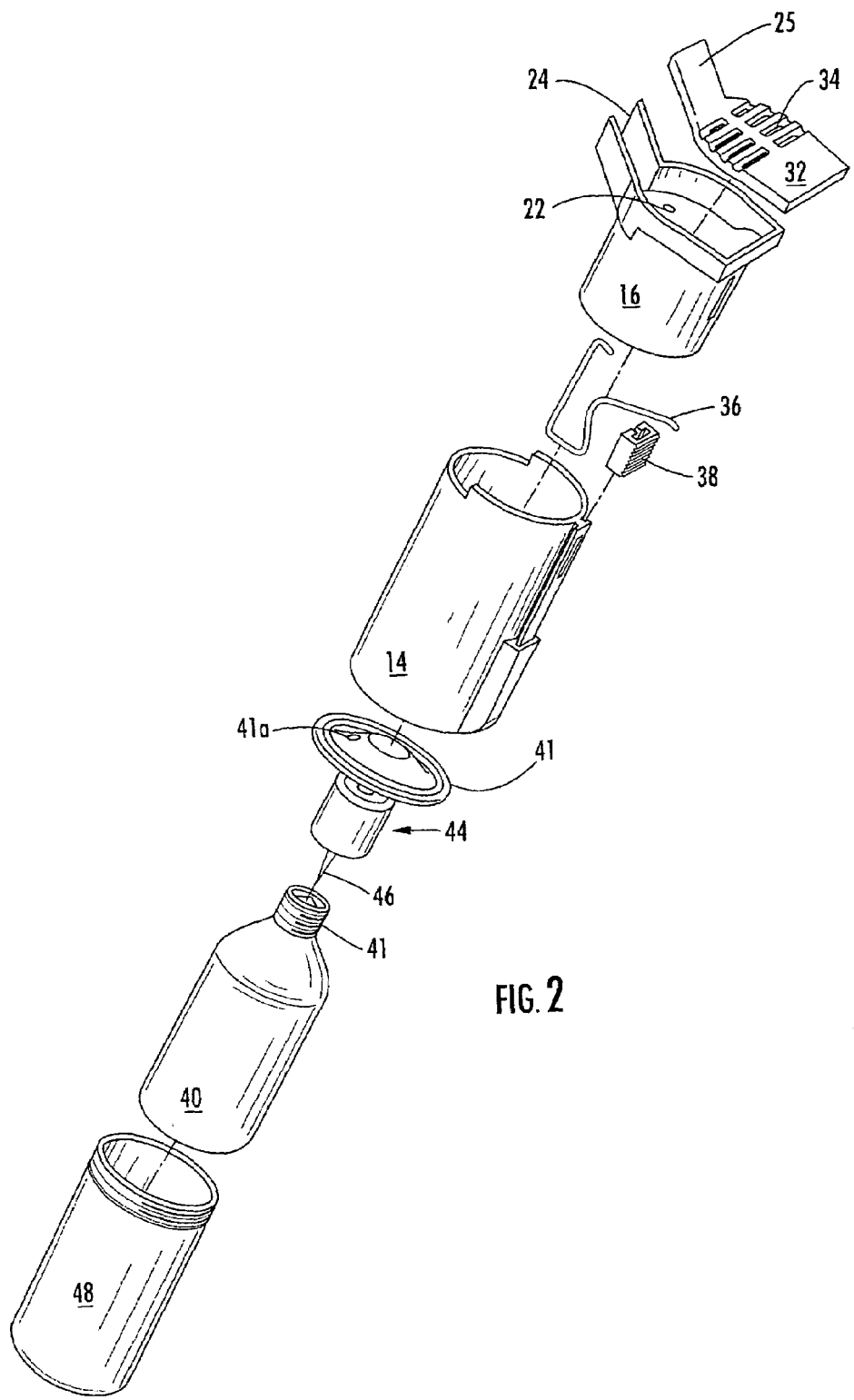
FIG. 2 is an exploded view of the portable gas delivery system.

FIG. 1 also illustrates a slide 38, which is utilized to activate the portable gas delivery system 10 to receive oxygen $O_2$ into the regulator 14. Operation of gas delivery system 10 including the slide 38 is described in greater detail below. Referring now to FIG. 2, the embodiment shown in FIG. 1 is seen in an exploded perspective view in which the cap 32 is attachable by snap or slide-fit or other conventional manner to the mixing chamber 20 and the outlet 24. The cap 32 as shown has a complementary outlet cover 25. The mixing chamber 20, outlet 24 and cap 32 may be unitarily constructed by blow-molding, injection molding, press-forming and similar processes. Therefore, the outlet 24 can be formed as a closed tube on the accumulator chamber 16 and the cap 32 can be substantially circular without the outlet cover 25. Additionally, the mixing chamber 20, outlet 24 and cap 32 may be wood, metal, ceramic, plastic, polymers or the like and be attached in a variety of ways to each other as stated.

Also seen in FIG. 2, the vent 22 is interposed between the accumulator chamber 16 and the mixing chamber 20 for the transfer of oxygen $O_2$ or other gas to the mixing chamber 20. The cap 32 and accumulator chamber 16 slidingly fit into the regulator 14 in this embodiment. Alternatively, the accumulator chamber 16 can be unitarily constructed with the regulator 14. In that event, the breathing outlet component 18 would snap, screw or slide on the regulator body 15.

A spring 36 is operatively disposed within the regulator 14 in FIG. 2. The slide 38 controllably contacts the spring 36 to activate a valve 44, which will be described in detail below. It is to be noted that the spring 36, slide 38, and valve 44 are provided by way of examples and are not intended as limitations of the present invention. For example, other activating mechanisms, such as a plunger, dial, push-button, or similar device can be used in place of the spring 36 and slide 38. Moreover, as will be described below, the valve 44, which is a Strater valve in this example, may be suitably interchanged with a disc-type or ball-type valve assembly and remain within the scope of the invention.

FIG. 2 further shows the cartridge 40 insertable in the regulator 14 where the cartridge 40 is accessed by a pin 46 for its contents. The cartridge 40 defines threads 41 for being threadingly received by a receiver 42 which has complementary threads 42a (see also FIG. 3). It is within the scope of the invention that the cartridge 40 be attached to the receiver 42 in other manners such as snap-fitting, press-fitting or the like. As the cartridge 40 is received into the receiver 42, a portion of the cartridge 40 is pierced by the pin 46. In this example, the threading action as the cartridge 40 is threaded into the receiver 42 causes the cartridge 40 to be pressed into the pin 46 and pierced in order for the contents of the cylinder 40 to be accessed. Once the contents of the cartridge 40 are expended, it is intended that the cartridge 40 be replaced with a similar cartridge 40 for continued use of the oxygen delivery system 10.

Also shown in FIG. 2, the cartridge cover 48 may be snap-fitted, screwed or attached to the regulator body 15 in any conventional manner. The cartridge cover 48 is between 3 to about 6 inches high and from between 1.5 inches to about 2.5 inches in diameter. These dimensions are ideally suited for carrying the oxygen delivery system 10 in a user's pocket. However, the invention is not limited to these specific sizes. Therefore, it is intended that larger or smaller cartridges 40 and cartridge covers 48 be utilized as desired.

The cover 48 is shown complementary shaped with respect to the cartridge 40. However, the cover 48 may be other shapes for protective and/or aesthetic purposes. Also, both the regulator body 15 and the cover 48 may be various colors.

Figure 3:
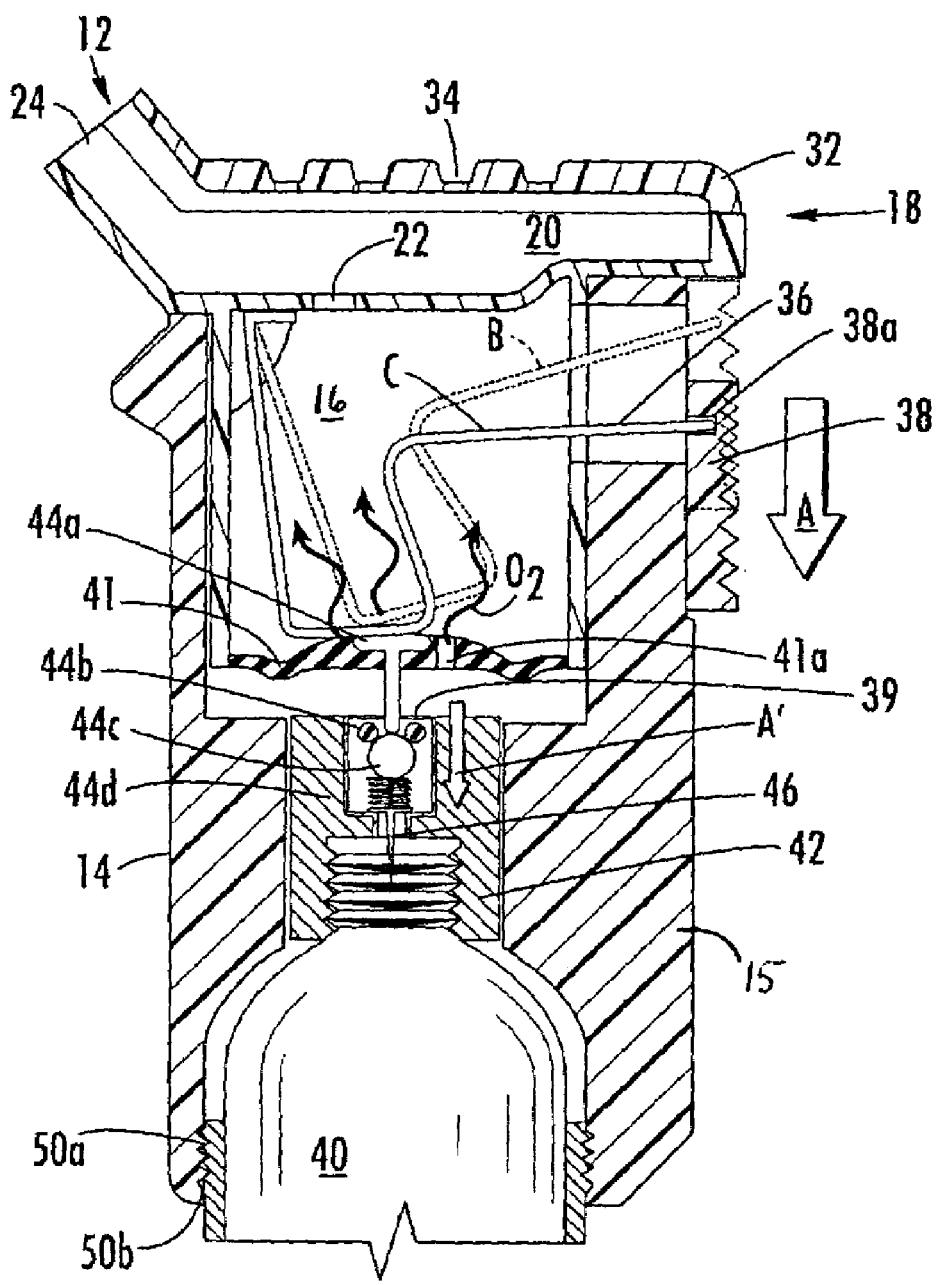
FIG. 3 is a partial side-view of the embodiment shown in FIG. 1, particularly showing an accumulator chamber within a regulator after execution of an axial movement of a slide translated into an axial movement of a valve according to an aspect of the invention.

FIG. 3 shows a partial but more developed view of the oxygen delivery system 10. This illustration shows accumulator chamber 16 and cap 32 forming outlet 24 as described above through which the gaseous contents are inhaled. As seen in FIG. 3, the valve 44 is the previously introduced Strater valve which includes in pertinent part a plunger 44a, an o-ring 44b, a ball 44c and a helical spring 44d. The spring 44d is interposed between the ball 44c and the pin 46. The pin 46 is shown piercing a portion of the cartridge 40 to access its gaseous contents and is designed to permit the gaseous contents to constantly flow in a direction of chamber openings 39. A diaphragm 41 is disposed about a portion of the plunger 44a such that as the plunger 44a is depressed, as described below, the gaseous contents flow through the chamber openings 39.

Finally, FIG. 3 shows a portion of the optional cover 48 attached to the regulator body 15 via attachment threads 50a which screwingly attach to complementary attachment threads 50b of the regulator 14. As suggested above, other suitable attachments such as snap-fits may be used in place of or in addition to attachment threads 50a and complementary attachment threads 50b. Further detail is not required to understand this aspect of the invention.

Figure 4:
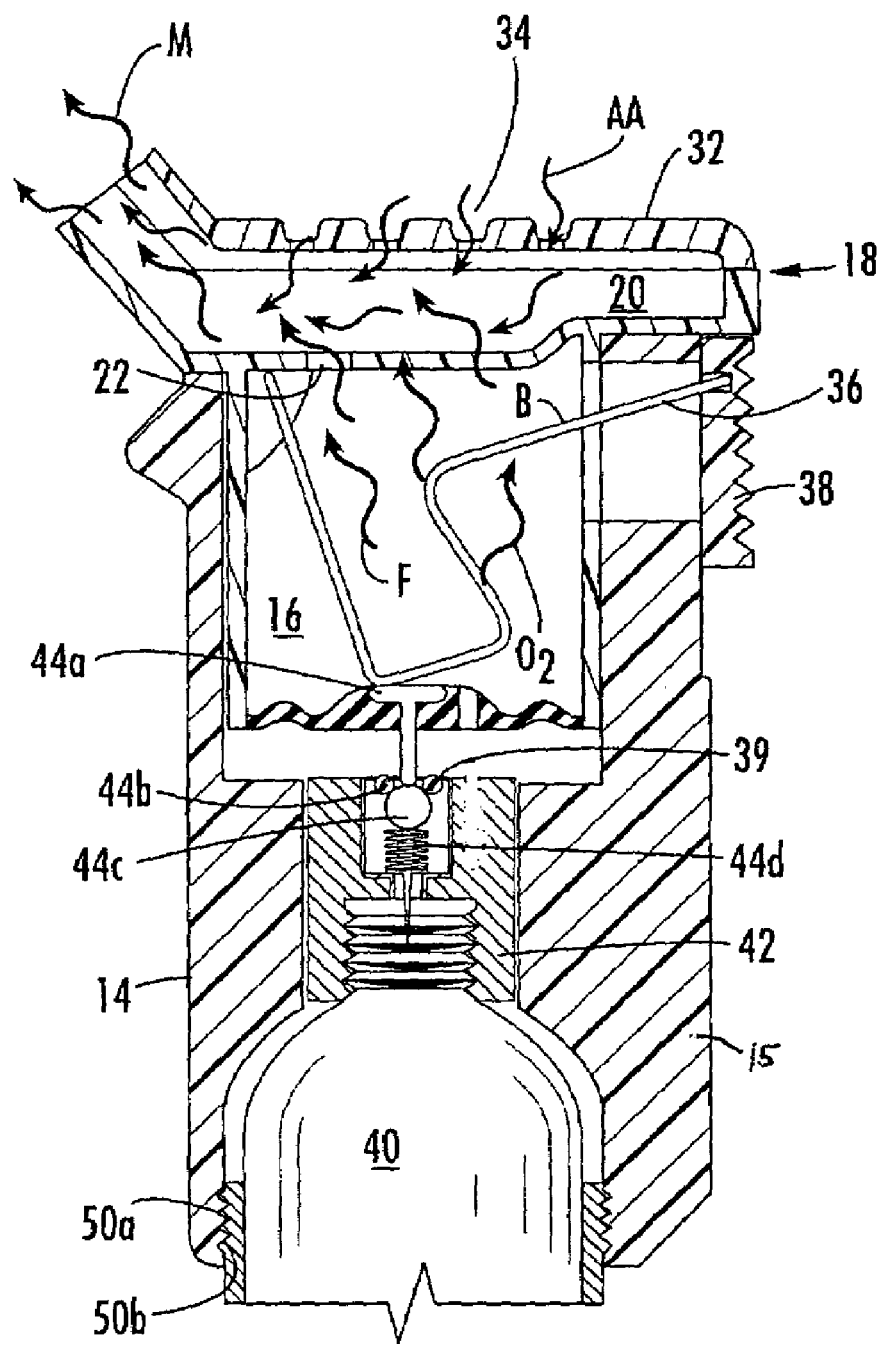
FIG. 4 is a side-view similar to FIG. 3 illustrating a manner in which gases are mixed in a mixing chamber according to an aspect of the invention.

Referring to both FIGS. 3 and 4, the oxygen delivery system 10 is easily placed in operation by sliding the slide 38 axially, substantially in parallel to the regulator body 15, in the direction of the arrow A. FIG. 3 particularly shows that the spring 36 is operatively attached to the slide 38 via a spring holder 38a. Therefore, as the user slides the slide 38, the spring 36 is displaced axially and laterally from its resting position B (shown in phantom in FIG. 3) to an operative position C. In this manner, the spring 36 causes the plunger 44a to be axially displaced, which in turn deformably displaces the diaphragm 41 and compresses the helical spring 44d. The compressed helical spring 44d, in this example, allows the o-ring 44b to be displaced in a direction A' away from the chamber openings 39. Generally, Strater valve operation is known and is therefore not described further.

The diaphragm 41 defines at least one hole 41a through which the gaseous contents flow from the cylinder 40 into the accumulator chamber 16 to achieve a regulated flow of the gaseous contents. More specifically, as the plunger 44a is axially displaced and deformably displaces the diaphragm 41, the hole 41a serves to regulate the flow of the gaseous contents at a constant gas pressure of 1–2.5 liters per minute (lpm) in this aspect. The diaphragm 41 in this example can be made of rubber or any deformable material. Moreover, the hole 41a can be a plurality of holes having various diameters, shapes, and placements about the diaphragm 41 to regulate the gaseous contents at various flow rates such as about 0.25 lpm to about 25 lpm under various pressures. Further, it is to be understood that the invention is not limited to the diaphragm 41. Any suitable arrangement for controlling the flow of the gaseous contents from the cylinder 40 is contemplated. These arrangements include ventilators, hoppers, disks with fixed or variable openings and similar devices to control gas flow.

With further reference to FIGS. 3 and 4, as the user continues to axially displace the slide 38 in direction A, oxygen $O_2$ from the cylinder 40 (indicated as wavy arrows) enters the accumulator chamber 16. The oxygen $O_2$ collects in the accumulator chamber 16, which here, is about 2 cubic inches in size.

It is to be noted that the embodiment described above requires the user to slide the slide 38, for instance, with a thumb in order to allow oxygen $O_2$ to enter the accumulator chamber 16. This operation can last an undetermined amount of time, even until the cartridge 40 is emptied, or for random sporadic durations. In other words, based on the user holding the slide 38 in a operative position C, the accumulator chamber 16 may be discretely filled with oxygen $O_2$ as regulated by the diaphragm 41 and hole 41a as described above. However, the invention also contemplates a predetermined release of oxygen $O_2$. For instance, the slide 38 can be constructed to cause the valve 44 to compress the helical spring 44d only for a discrete period to allow only a discrete amount of oxygen $O_2$ into the accumulator chamber 16.

Moreover, a rotary dial-type mechanism may be used in place of slide 38 to preset a desired or metered dosage of the contents of the cartridge 40.

With reference to FIG. 4, the user has released the slide 38 from the operative position C in FIG. 3 and has inhaled through the mouthpiece 12. In this example, the action of inhaling causes the oxygen $O_2$ to enter the mixing chamber 20 through the vent 22. Simultaneously, an ambient air AA is delivered through one or more breather slots 34 into the mixing chamber 20. The action of inhaling also mixes the ambient air AA and the oxygen $O_2$ into a mixed air M in the mixing chamber 20. The mixed air M is then delivered through the outlet 24 to the user.

The breather slots 34 just described are illustrated as substantially rectangular slots (see also FIG. 2); however, the breather slots 34 may be different shapes and may have different sizes such as circular, oval, square, or the like. Moreover, the breather slots 34 can have various geometries and sizes. For example, randomly spaced circular slots can be intermixed and adjacent to randomly placed square slots.

With continued reference to FIG. 4, it is to be noted that a flavorant F can be added to the cartridge 40 and thereby mixed as a gaseous or particulate flavorant with the oxygen $O_2$. The flavorant F can be orange, lemon-lime, grape, cherry, strawberry, peppermint, mint, spearmint, licorice, bubble-gum, blackberry, blueberry, apple, banana, kiwi, lime, lemon, watermelon, piná colada, or any flavor as requested by users.

It will be apparent to those skilled in the art that various modifications and variations can be made in the present invention without departing from the scope and spirit of the invention. For example, specific shapes of various elements of the illustrated embodiments may be altered to suit particular applications. It is intended that the present invention include such modifications and variations as come within the scope of the appended claims and their equivalents.

That which is claimed is:

1. A portable gas delivery system, comprising:
   a regulator having a mixing chamber and an accumulator chamber therein, the accumulator chamber being at least 0.2 cubic inches in volume;
   a cartridge attachable to the regulator, the cartridge containing a gas and configured to deliver the gas to the accumulator chamber at a flow rate of at least about 1.5 liters per minute, the mixing chamber in gaseous communication with the accumulator chamber and configured to form a gaseous mixture with the gas from the accumulator chamber by mixing in an ambient air;
   means for filling the accumulator chamber with the gas; and
   an outlet in communication with the mixing chamber, the outlet being configured to deliver the gaseous mixture from the mixing chamber.

2. The gas delivery system of claim 1, wherein the gas is oxygen and a flavorant.

3. The gas delivery system of claim 1, wherein the means for filling the accumulator chamber includes a regulating diaphragm defining a hole therethrough and biasing means for biasing valve means for opening and filling the accumulator chamber with the gas via the hole.

4. The gas delivery system of claim 3, wherein the biasing means for biasing is a spring and a slide mechanism, the spring disposed within the regulator and operably connected to the slide mechanism such that operation of the slide mechanism presses the spring against the valve means to open the accumulator chamber.

5. The gas delivery system of claim 1, wherein the means for filling the accumulator chamber includes a metering mechanism configured to deliver a metered dosage of the gas to the accumulator chamber.

6. An individual use gas delivery system, comprising:
   a regulator having an accumulator chamber and a breathing outlet component, the accumulator being at least 0.15 cubic inches in volume, the breathing outlet component disposed adjacent the accumulator chamber;
   a replaceable cartridge attachable to the regulator, the accumulator chamber configured to receive a quantity of oxygen from the cartridge, the breathing outlet component configured to form a gaseous mixture with the oxygen from the accumulator chamber and ambient air disposed about the gas delivery system, the breathing outlet component having an outlet therein to deliver the gaseous mixture to a user; and
   a valve assembly attached to the regulator and configured for filling the accumulator chamber.

7. The gas delivery system of claim 6, wherein the breathing outlet component includes a mixing chamber therein with a vent therethrough configured to receive the oxygen from the accumulator chamber.

8. The gas delivery system of claim 6, wherein the oxygen is mixed with a flavorant selected from the group consisting of orange, lemon-lime, grape, cherry, strawberry, peppermint, mint, spearmint, licorice, bubble-gum, blackberry, blueberry, apple, banana, kiwi, lime, lemon, watermelon, piná colada, and combinations thereof.

9. The gas delivery system of claim 6, wherein the valve assembly is a manually operated valve assembly including a spring and a slide mechanism configured to open the accumulator chamber, the spring being configured to urge closed the accumulator chamber.

10. The gas delivery system of claim 6, wherein the valve assembly is a metering mechanism configured to deliver a metered dosage of the oxygen to the accumulator chamber.

* * * * *